(12) United States Patent
Shigenoi

(10) Patent No.: US 11,400,026 B2
(45) Date of Patent: Aug. 2, 2022

(54) LAMINATE, KIT, AND METHOD FOR PRODUCING LAMINATE

(71) Applicant: FUJIFILM Corporation, Tokyo (JP)

(72) Inventor: Yuta Shigenoi, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 272 days.

(21) Appl. No.: 16/675,412

(22) Filed: Nov. 6, 2019

(65) Prior Publication Data

US 2020/0069531 A1    Mar. 5, 2020

Related U.S. Application Data

(63) Continuation of application No. PCT/JP2018/018095, filed on May 10, 2018.

(30) Foreign Application Priority Data

May 16, 2017   (JP) .............................. JP2017-097090
Dec. 27, 2017   (JP) .............................. JP2017-250727

(51) Int. Cl.
*A61K 6/20* (2020.01)
*A61C 13/02* (2006.01)
*C09D 133/10* (2006.01)
*C09D 133/14* (2006.01)
*C09D 133/26* (2006.01)
*C09D 135/00* (2006.01)

(52) U.S. Cl.
CPC ................ *A61K 6/20* (2020.01); *A61C 13/02* (2013.01); *C09D 133/10* (2013.01); *C09D 133/14* (2013.01); *C09D 133/26* (2013.01); *C09D 135/00* (2013.01)

(58) Field of Classification Search
None
See application file for complete search history.

(56) References Cited

U.S. PATENT DOCUMENTS

| | | | |
|---|---|---|---|
| 4,648,845 A | 3/1987 | Orlowski et al. | |
| 4,806,381 A | 2/1989 | Engelbrecht et al. | |
| 4,872,936 A | 10/1989 | Engelbrecht | |
| 10,494,540 B2 | 12/2019 | Fukagawa | |
| 2003/0055124 A1* | 3/2003 | Klee | A61K 6/30 523/120 |
| 2003/0069327 A1* | 4/2003 | Walz | A61K 6/54 523/116 |
| 2004/0171716 A1* | 9/2004 | Walz | A61K 6/887 523/105 |
| 2006/0246017 A1* | 11/2006 | Klee | C07F 9/091 424/57 |
| 2007/0027229 A1* | 2/2007 | Moszner | A61K 6/30 523/109 |
| 2013/0103157 A1* | 4/2013 | Kourtis | C08G 18/6705 206/568 |
| 2017/0362458 A1* | 12/2017 | Cheng | C07C 227/16 |
| 2018/0142119 A1* | 5/2018 | Fukagawa | C08K 5/19 |
| 2018/0296445 A1* | 10/2018 | Amao | C08K 3/22 |
| 2019/0290551 A1* | 9/2019 | Yamamoto | C09D 4/00 |
| 2020/0069531 A1* | 3/2020 | Shigenoi | C09D 135/00 |

FOREIGN PATENT DOCUMENTS

| | | |
|---|---|---|
| JP | 62-149707 A | 7/1987 |
| JP | 62-149715 A | 7/1987 |
| JP | 2015-209421 A | 11/2015 |
| JP | 2017-002171 A | 1/2017 |
| WO | 2017/018146 A1 | 2/2017 |
| WO | 2017/135186 A1 | 8/2017 |

OTHER PUBLICATIONS

IQSearchText (Year: 2022).*
Google scholar search (Year: 2022).*
Extended European Search Report dated Apr. 9, 2020 from the European Patent Office in European application No. 18802652.0.
Yan, S., et al., "Hierarchical Polymer Brushes with Dominant Antibacterial Mechanisms Switching from Bactericidal to Bacteria Repellent", Bio Macromolecules, vol. 17, No. 5, 2016, XP055529430, pp. 1696-1704.
International Search Report dated Aug. 14, 2018 from the International Searching Authority in counterpart International Application No. PCT/JP2018/018095.
International Preliminary Report on Patentability dated Nov. 4, 2019 from the International Bureau in counterpart International Application No. PCT/JP2018/018095.
Written Opinion dated Aug. 14, 2018 from the International Bureau in counterpart International Application No. PCT/JP2018/018095.
Office Action dated Dec. 1, 2020, from the Japanese Patent Office in Japanese Application No. 2019-519204.

* cited by examiner

*Primary Examiner* — Peter A Salamon
(74) *Attorney, Agent, or Firm* — Sughrue Mion, PLLC

(57) ABSTRACT

The present invention provides a laminate having excellent bacteria adhesion suppression performance. The present invention also provides a kit and a method for producing a laminate. A laminate according to the present invention includes a base material, an undercoat layer formed of an undercoat layer forming composition containing a polymer containing a repeating unit containing a polymerizable group and a repeating unit containing a polar group, and a cured film formed of a curable composition containing at least one compound selected from the group consisting of a compound represented by Formula (I), a compound represented by Formula (II), a compound represented by Formula (IV), and a compound represented by Formula (V) in this order.

16 Claims, No Drawings

LAMINATE, KIT, AND METHOD FOR PRODUCING LAMINATE

CROSS-REFERENCE TO RELATED APPLICATIONS

This application is a Continuation of PCT International Application No. PCT/JP2018/018095 filed on May 10, 2018, which claims priority under 35 U.S.C. § 119(a) to Japanese Patent Application No. 2017-097090 filed on May 16, 2017 and Japanese Patent Application No. 2017-250727 filed on Dec. 27, 2017. Each of the above applications is hereby expressly incorporated by reference, in its entirety, into the present application.

BACKGROUND OF THE INVENTION

1. Field of the Invention

The present invention relates to a laminate, a kit, and a method for producing a laminate.

2. Description of the Related Art

As a device that is transplanted or arranged in a human living body and placed in the body, artificial joints, artificial bones, artificial blood vessels, stents, dental implants, and denture bases are known. Such devices are required to prevent adhesion of contaminants in the body. As such a technique, JP2015-209421A describes "a dental composition containing (A) polymerizable monomer component that is zwitterionic, and (B) non-zwitterionic compound having a hydroxyl group and/or a non-zwitterionic compound capable of dissolving an inorganic salt".

SUMMARY OF THE INVENTION

The present inventors have conducted studies on bacteria adhesion suppression performance of a laminate which is obtained by forming a coating layer on a base material imitating a denture base using the dental composition described in JP2015-209421A and thus clarified that there is room for improvement.

Therefore, an object of the present invention is to provide a laminate having excellent bacteria adhesion suppression performance. Another object of the present invention is to provide a kit and a method for producing a laminate.

As a result of intensive studies to achieve the above-described objects, the present inventors have found that the above-described objects can be achieved by the following configurations.

[1] A laminate comprising, in order: a base material; an undercoat layer formed of an undercoat layer forming composition containing a polymer containing a repeating unit containing a polymerizable group and a repeating unit containing a polar group; and a cured film formed of a curable composition containing at least one compound selected from the group consisting of a compound represented by Formula (I) described later, a compound represented by Formula (II) described later, a compound represented by Formula (IV) described later, and a compound represented by Formula (V) described later.

[2] The laminate according to [1], in which a double bond equivalent of the polymer is 2000 or less.

[3] The laminate according to [1] or [2], in which the repeating unit containing a polymerizable group is a repeating unit represented by Formula (A1) described later.

[4] The laminate according to any one of [1] to [3], in which an acid value or a hydroxyl number of the polymer is 20 mgKOH/g or more.

[5] The laminate according to any one of [1] to [4], in which the curable composition contains at least one compound selected from the group consisting of the compound represented by Formula (I) and the compound represented by Formula (II), and at least one compound selected from the group consisting of the compound represented by Formula (IV) and the compound represented by Formula (V).

[6] The laminate according to [5], in which a content ratio of a total content of the compound represented by Formula (I) and the compound represented by Formula (II) with respect to a total content of the compound represented by Formula (IV) and the compound represented by Formula (V) is 10/90 to 90/10.

[7] The laminate according to any one of [1] to [6], in which the curable composition further contains a polymerization initiator.

[8] The laminate according to any one of [1] to [7], in which the base material is a denture base.

[9] A kit formed of an undercoat layer forming composition containing a polymer containing a repeating unit containing a polymerizable group and a repeating unit containing a polar group, and a curable composition containing at least one compound selected from the group consisting of a compound represented by Formula (I), a compound represented by Formula (II), a compound represented by Formula (IV) and a compound represented by Formula (V).

[10] A kit for producing the laminate according to any one of [1] to [8], which is formed of an undercoat layer forming composition containing a polymer containing a repeating unit containing a polymerizable group and a repeating unit containing a polar group, and a curable composition containing at least one compound selected from the group consisting of the compound represented by Formula (I), the compound represented by Formula (II), the compound represented by Formula (IV) and the compound represented by Formula (V).

[11] A method for producing a laminate to produce the laminate according to any one of [1] to [8], the method comprising: a step of forming a first coating film on the base material using an undercoat layer forming composition containing a polymer containing a repeating unit containing a polymerizable group and a repeating unit containing a polar group; a step of forming a second coating film on the first coating film using a curable composition containing at least one compound selected from the group consisting of the compound represented by Formula (I), the compound represented by Formula (II), the compound represented by Formula (IV) and the compound represented by Formula (V); and a step of applying energy to the first coating film and the second coating film and curing the films to obtain an undercoat layer and a cured film.

[12] The method for producing a laminate according to [11], in which the base material is a denture base.

According to the present invention, it is possible to provide a laminate having excellent bacteria adhesion suppression performance (hereinafter, also referred to as "having the effect of the present invention"). According to the present invention, it is also possible to provide a kit and a method for producing a laminate.

DESCRIPTION OF THE PREFERRED EMBODIMENTS

Hereinafter, the present invention will be described in detail.

The description of configuration requirements described below is made based on representative embodiments of the present invention. However, the present invention is not limited to such embodiments.

The numeric ranges expressed using "to" in the present specification include numerical values described before and after "to" as the lower limit value and the upper limit value.

In addition, in the present specification, "(meth)acryl" means acryl and methacryl. Also, in the present invention, "(meth)acryloyl" means acryloyl and methacryloyl.

[Laminate]

A laminate comprises, in order, a base material, an undercoat layer formed of an undercoat layer forming composition containing a polymer containing a repeating unit containing a polymerizable group and a repeating unit containing a polar group, and a cured film formed of a curable composition containing at least one compound selected from the group consisting of a compound represented by Formula (I) described later, a compound represented by Formula (II) described later, a compound represented by Formula (IV) described later, and a compound represented by Formula (V) described later. The laminate has excellent bacteria adhesion suppression performance. In the present specification, the bacteria adhesion suppression performance means the performance of the laminate to be evaluated by the method described in Examples.

The reason why the laminate has excellent bacteria adhesion suppression performance is not necessarily clear, but the present inventors assume as follows. The scope of the present invention is not limited by the following assumptions, and those that can obtain effects by mechanisms other than the following assumptions are also included in the scope of the present invention.

In a case where the laminate is transplanted or arranged in a human living body and placed in the body, it is considered that the laminate is always placed in a wet environment. For example, in a case where the base material of the laminate is a denture base, the laminate is exposed to saliva, and food and drink. According to the studies by the present inventors, it has been found that in a case where a laminate is prepared by forming a coating layer on the base material imitating a denture base using the dental composition described in JP2015-209421A, a part of the coating layer is peeled off in a wet environment, and expected bacteria adhesion suppression performance is not exhibited.

The laminate according to the embodiment of the present invention has an undercoat layer having a predetermined structure between the cured film and the base material. Therefore, it is assumed that the cured film and the base material are further closely attached, the cured film is not easily peeled off even in a case where the laminate is placed in a wet environment, and as a result, the laminate has excellent bacteria adhesion suppression performance, specifically, excellent bacteria adhesion suppression performance to bacteria in the in the mouth, particularly, Candida, caries-causing bacteria, and periodontal bacteria (for example, *Streptococcus mutans, Streptococcus sobrinus, Lactobacillus,* and *Actinomyces naeslundii*), and periodontal disease bacteria (for example, *Porphyromonas gingivalis, Tannerella forsythensis, Treponema denticola, Prevotella intermedia, Actinobacillus actinomycetemcomitans, Aggregatibacter actinomycetemcomitans,* and *Fusobacterium nucleatum*). Hereinafter, the members and components of the above laminate will be described.

[Base Material]

The base material is not particularly limited and a known base material can be used.

Examples of the base material include inorganic materials, organic materials, and composite materials thereof.

Examples of organic materials include (meth)acrylic resins, polyethylene sulfone resins, polyacetal resins, cycloolefin resins, silicone resins, polyamide resins, and polycarborate resins, and among these, from the viewpoint of having excellent durability and excellent workability, (meth)acrylic resins are preferable.

Examples of inorganic materials include gold, platinum, palladium, copper, mangan, silicon, molybdenum, zinc, tin, iridium, cobalt, chromium, titanium, and alloys thereof, aluminum, zirconia, hydroxyapatite, β-tricalcium phosphate (β-TCP), dicalcium phosphate dehydrate, octacalcium phosphate, and tetracalcium phosphate.

The shape and size of the base material can be changed appropriately according to the application. For example, in a case where the base material is a denture base, the base material may be either a partial base or a whole base.

[Undercoat Layer]

The laminate comprises an undercoat layer formed of an undercoat layer forming composition containing a polymer containing a repeating unit containing a polymerizable group and a repeating unit containing a polar group on the base material. The undercoat layer has a function of closely attaching both the base material and a cured film described later therebetween. The undercoat layer included in the laminate according to the embodiment of the present invention is capable of stably closely attaching the base material and the cured film for a long period of time particularly even in a wet environment in a living body.

The undercoat layer is formed of an undercoat layer forming composition. The undercoat layer is preferably formed by performing a curing treatment on the coating film of the undercoat layer forming composition (first coating film).

Although the details will be described in detail later, typically, the undercoat layer forming composition is applied to the base material to form a first coating film, a second coating film obtained by applying a curable composition described later is laminated on the first coating film, and energy (heat or light) is applied to the both coating films to cure the films. Thus, the undercoat layer is obtained from the first coating film.

The thickness of the undercoat layer in the laminate is not particularly limited and can be determined appropriately according to the use of the laminate. For example, in a case where the base material is a denture base, the thickness of the undercoat layer is not particularly limited, and is preferably 0.1 to 10 μm.

<Undercoat Layer Forming Composition>

The undercoat layer forming composition contains a polymer containing a repeating unit containing a polymerizable group and a repeating unit containing a polar group.

The content of the polymer in the undercoat layer forming composition is not particularly limited, and is preferably 0.001% to 99.9% by mass and more preferably 0.01% to 20% by mass with respect to the total mass of the undercoat layer forming composition. The polymer may be used alone or in combination of two or more kinds thereof. In a case where two or more kinds of polymers are used in combination, the total content is preferably within the above range.

(Polymer)

The polymer contains a repeating unit containing a polymerizable group (hereinafter, also referred to as a "unit A") and a repeating unit containing a polar group (hereinafter, also referred to as a "unit B").

In addition, the polymer may contain another unit (hereinafter, also referred to as a "unit C").

The content of each repeating unit in polymer is not particularly limited and from the viewpoint that a laminate having the more excellent effect of the present invention can be obtained, the content of the unit A with respect to all the repeating units of the polymer is preferably 0.1% to 99.9% by mole and more preferably 5% to 99% by mole.

In addition, from the viewpoint that a laminate having the more excellent effect of the present invention can be obtained, the content of the unit B with respect to all the repeating units of the polymer is preferably 0.1% to 99.9% by mole and more preferably 1% to 95% by mole.

Particularly, in a case where the polymer formed of the unit A and the unit B, the content of each unit is preferably within the above range.

In addition, in a case where the polymer contains the unit A, the unit B, and the unit C, from the viewpoint that a laminate having the more excellent effect of the present invention can be obtained, the content of the unit A with respect to all the repeating units of the polymer is preferably 0.1% to 99.8% by mole and more preferably 5.0% to 98% by mole, the content of the unit B is preferably 0.1% to 99.8% by mole and more preferably 1.0% to 94% by mole, and the content of the unit C is preferably 0.1% to 99.8% by mole and more preferably 1.0% to 90% by mole.

Particularly, in a case where the polymer is formed of the unit A, the unit B, and the unit C, the content of each unit is preferably within the above range.

The acid value and the hydroxyl number of the polymer are not particularly limited, and from the viewpoint that a laminate having the more excellent effect of the present invention can be obtained, the acid value or the hydroxyl number is preferably 5 mgKOH/g or more and more preferably 20 mgKOH/g or more. The upper limit of the acid value and the hydroxyl number is not particularly limited, and is preferably 200 mgKOH/g or less.

In the present specification, the acid value and the hydroxyl number means an acid value and a hydroxyl number measured by the method described in JIS K0070. That is, the acid value is expressed in mg of potassium hydroxide (unit: mgKOH/g) required to neutralize the acid groups contained in 1 g of polymer. The hydroxyl number is expressed in mg of potassium hydroxide (mgKOH/g) required to neutralize acetic acid bonded to hydroxyl groups when 1 g of polymer is acetylated.

The polymer contained in the undercoat layer forming composition can be separated by preparative gel permeation chromatography (GPC) method.

The molecular weight of polymer is not particularly limited, and the weight-average molecular weight (Mw) is preferably 1000 to 1000000.

In the present specification, Mw can be measured by the GPC method and can be obtained in terms of standard polystyrene. Specifically, for example, for GPC, HLC-8220 GPC (manufactured by Tosoh Corporation) is used, TSKgeL Super HZ4000 (manufactured by Tosoh Corporation, 4.6 mmID×15 cm) is used as a column, and tetrahydrofuran (THF) is used as an eluent. In addition, as conditions, the sample concentration is 0.02% by mass, the flow rate is 0.35 ml/min, the sample injection amount is 10 μl, the measurement temperature is 40° C., and an infrared (IR) detector is used. In addition, a calibration curve is prepared from 8 samples of "Standard Sample TSK standard, polystyrene" manufactured by Tosoh Corporation: "F-40", "F-20", "F-4", "F-1", "A-5000", "A-2500", "A-1000", and "n-propylbenzene".

The double bond equivalent of the polymer is not particularly limited and from the viewpoint that a laminate having the more excellent effect of the present invention can be obtained, the double bond equivalent is preferably 4000 or less and more preferably 2000 or less. The lower limit of the double bond equivalent is not particularly limited, and is preferably 100 or more.

In a case where the double bond equivalent is 2000 or less, the cured film is not easily peeled off even in a case where the laminate is placed in a wet environment (the undercoat layer has the more excellent adhesiveness).

In the present specification, the double bond equivalent means the weight-average molecular weight of the polymer with respect to the number of double bonds contained in one molecule of the polymer.

First, the weight-average molecular weight of the polymer is obtained by the above method.

Next, the number of double bonds is calculated according to the iodine value measurement method described in JIS K0070: 1992. That is, the weight-average molecular weight is obtained such a manner that the number of C=C bonds in the polymer is calculated from the mass of iodine added to the polymer. The method of separating the polymer from the undercoat layer forming composition is as described above. The double bond equivalent is expressed by the following equation.

(Equation) (double bond equivalent)=(weight-average molecular weight of polymer)/(number of double bonds)

Unit A

The polymerizable group contained in the unit A is not particularly limited, and examples thereof include addition polymerization reactive groups such as an alkenyl group and an alkynyl group. Examples of the alkenyl group include a vinyl group, a propenyl group, an allyl group, a butenyl group, and a dialkyl maleimide group. Examples of the alkynyl group include an acetylene group and an alkylacetylene group. Among these, from the viewpoint that a laminate having the more excellent effect of the present invention can be obtained, as the polymerizable group, a vinyl group, a propenyl group, an allyl group, an acryl group which is a derivative of a vinyl group, or a methacryl group which is a derivative of a propenyl group is preferable.

The unit A is preferably represented by Formula (A1).

(A1)

In Formula (A1), $R_{1A}$, $R_{2A}$, and $R_{3A}$ each independently represent one group selected from the group consisting of a hydrogen atom, an alkyl group having 1 to 6 carbon atoms, and a halogen atom, $R_{4A}$ to $R_{6A}$ each independently represent one group selected from the group consisting of a hydrogen atom, an alkyl group having 1 to 6 carbon atoms, a halogen atom, an acyl group, and an acyloxy group, $R_{4A}$ and $R_{5A}$ or $R_{5A}$ and $R_{6A}$ may each form a ring, and L represents one group selected from the group consisting of —CO—, —O—, —NH—, a divalent aliphatic group, a divalent aromatic group, and a divalent linking group obtained by combining these groups.

Specific examples of the "divalent linking group obtained by combining these groups" represented by L are shown below. In the examples below, the left side is bonded to the main chain of the polymer, and the right side is bonded to the ethylenically unsaturated bond.

L1: —CO—NH-divalent aliphatic group-O—CO—
L2: —CO-divalent aliphatic group-O—CO—
L3: —CO—O-divalent aliphatic group-O—CO—
L4: -divalent aliphatic group-O—CO—
L5: —CO—NH-divalent aromatic group-O—CO—
L6: —CO-divalent aromatic group-O—CO—
L7: -divalent aromatic group-O—CO—
L8: —CO-divalent aliphatic group-CO—O-divalent aliphatic group-O—CO—
L9: —CO-divalent aliphatic group-O—CO-divalent aliphatic group-O—CO—
L10: —CO-divalent aromatic group-CO—O-divalent aliphatic group-O—CO—
L11: —CO-divalent aromatic group-O—CO-divalent aliphatic group-O—CO—
L12: —CO-divalent aliphatic group-CO—O-divalent aromatic group-O—CO—
L13: —CO-divalent aliphatic group-O—CO-divalent aromatic group-O—CO—
L14: —CO-divalent aromatic group-CO—O-divalent aromatic group-O—CO—
L15: —CO-divalent aromatic group-O—CO-divalent aromatic group-O—CO—
L16: —CO—O-divalent aliphatic group—

Examples of the divalent aliphatic group include an alkylene group that may contain a substituent, an alkenylene group that may contain a substituent, and an alkynylene group that may contain a substituent.

Examples of the divalent aromatic group include an arylene group which may contain a substituent.

In the present specification, a unit containing both a polymerizable group and a polar group described later corresponds to the unit A and does not correspond to the unit B.

Unit B

The polar group contained in the unit B is not particularly limited and known polar groups may be used. Examples thereof include an amino group, a carboxy group, and hydroxy. Among these, from the viewpoint that a laminate having the more excellent effect of the present invention can be obtained, an interactive group having an interaction with the base material is preferable. Examples of interactions include an ion bond, a hydrogen bond, a coordination bond, and a bond due to an intermolecular force between the base material and the interactive group.

As an interactive group, for example, an acid group or an onium group can be used. As the acid group, a group having an acid dissociation constant (pKa) of 7 or less is preferable, and examples thereof include a carboxy group, —SO$_3$H, —OSO$_3$H, —PO$_3$H$_2$, —OPO$_3$H$_2$, —CONHSO$_2$—, and —SO$_2$NHSO$_2$—.

As the onium group, an onium group formed from an atom belonging to Group 5B (Group 15) or Group 6B (Group 16) of the periodic table may be used, and an onium group formed from a nitrogen atom, a phosphorus atom or a sulfur atom is preferable.

As the interactive group, a carboxy group, a hydroxy group, —PO$_3$H$_2$, or —PO$_3$H$_2$ is preferable.

Unit C

The polymer may contain another unit C as a repeating unit other than the units A and B as long as the effect of the present invention is not impaired. In the present specification, the unit C intends a repeating unit different from both the unit A and the unit B.

The unit C is not particularly limited, and from the viewpoint that a laminate having the more excellent effect of the present invention can be obtained, a repeating unit represented by Formula (C) below is preferable.

(C)

In Formula (C), each form of $R_{1A}$ to $R_{3A}$ is the same as each symbol in Formula (A1).

L represents a single bond or one group selected from the group consisting of —CO—, —O—, —NH—, a divalent aliphatic group, a divalent aromatic group, and a divalent linking group obtained by combining these groups. The form of the divalent linking group is as described in Formula (A1).

In Formula (C), W represents a group represented by the following formula.

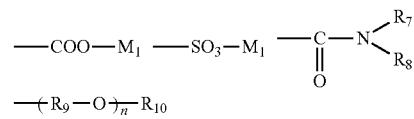

In the above formula, $M_1$ represents an alkyl group, a metal atom, or an ammonium group. $R_7$ and $R_8$ each independently represent a hydrogen atom or a linear or branched alkyl group having 1 to 6 carbon atoms. $R_9$ represents a linear or branched alkylene group having 1 to 6 carbon atoms. $R_{10}$ represents a hydrogen atom or an alkyl group having 1 to 12 carbon atoms. n represents an integer from 1 to 100.

Examples of the polymer are shown below, but the polymer contained in the undercoat layer included in the laminate according to the embodiment is not limited to the following. In the following formula, x, y, and z represent the copolymerization ratios (% by mole).

In a case where x and y exist in the formula, 0<x<100, 0<y<100, and x+y=100 (% by mole) are established. In a case where x, y, and z exist in the formula, 0<x<100, 0<y<100, 0<z<100, and x+y+z=100 (% by mole) are established.

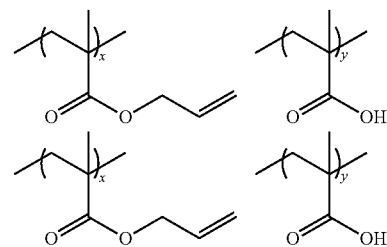

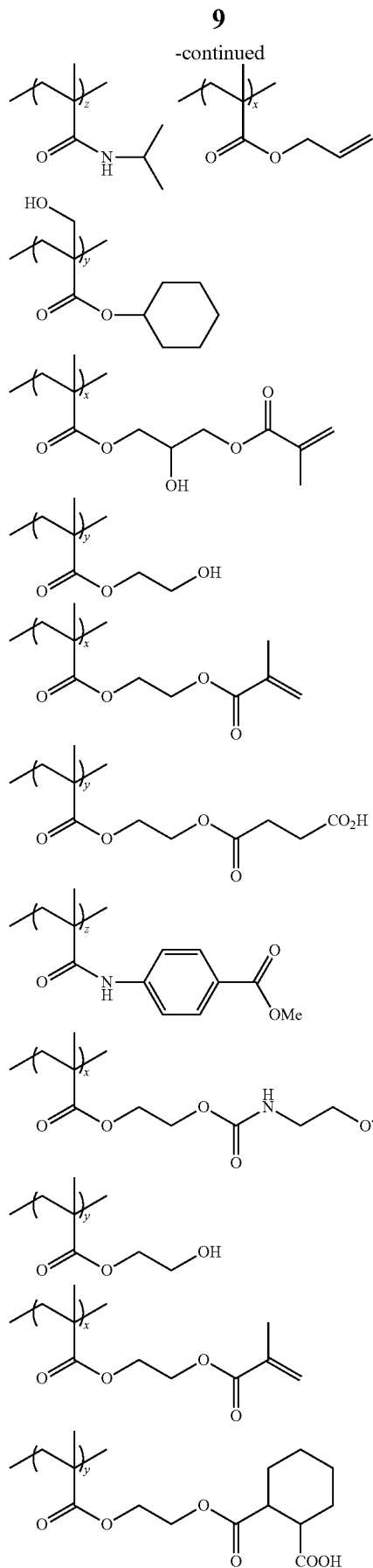
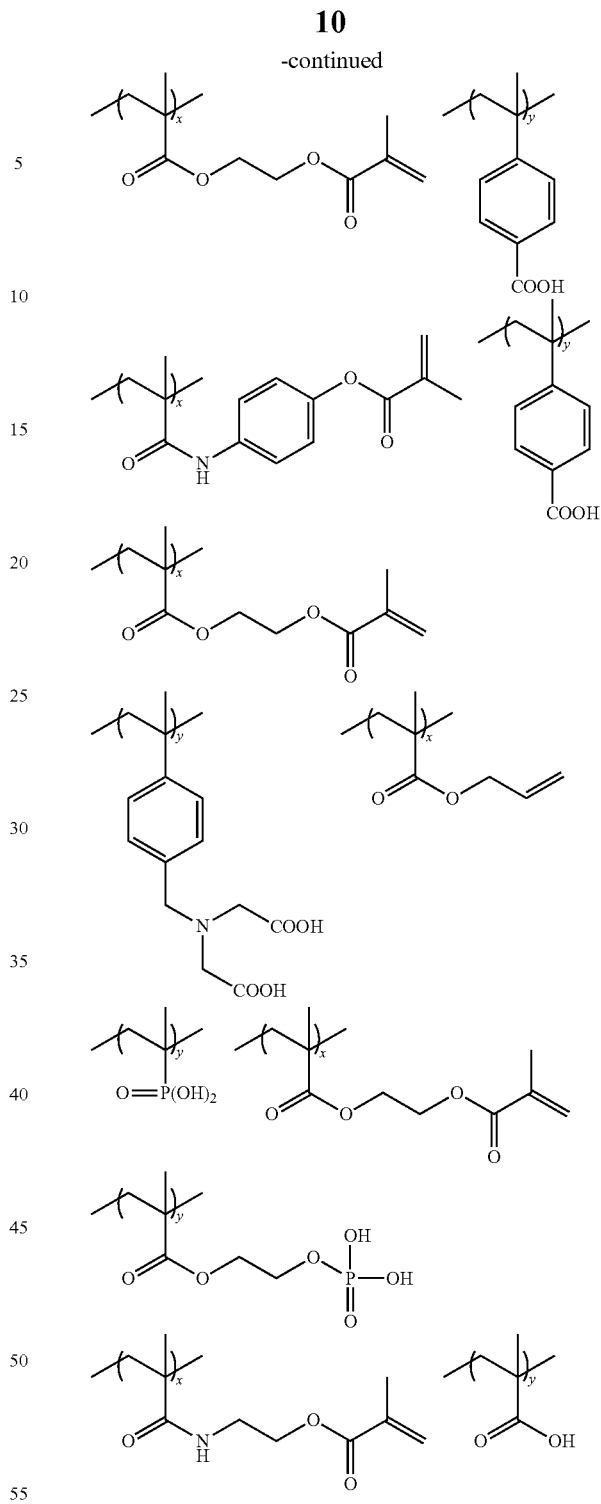

(Other Components)

The undercoat layer forming composition may contain components other than the polymer. Examples of components other than the polymer include a solvent, and a polymerization initiator.

The solvent is not particularly limited, and water, known organic solvents, or a mixture thereof can be used. Examples of organic solvents include methanol, ethanol, and methyl ethyl ketone.

The solid content of the undercoat layer forming composition is not particularly limited, and from the viewpoint that the undercoat layer can be more easily formed, is preferably 0.001% to 99.9% by mass and more preferably 0.01% to 20% by mass.

The solid content means a component that can form an undercoat layer and does not contain a solvent.

Polymerization Initiator

The undercoat layer forming composition preferably contains a polymerization initiator.

The content of the polymerization initiator in the undercoat layer composition is not particularly limited, and is preferably 0.01% to 50% by mass with respect to the total mass of the undercoat layer forming composition. The polymerization initiator may be used alone or in combination of two or more kinds thereof. In a case where two or more kinds of polymerization initiators are used in combination, the total content is preferably within the above range.

A known polymerization initiator can be used and is not particularly limited. As the polymerization initiator, for example, the same polymerization initiator as that contained in the curable composition described later can be used.

[Cured Film]

The laminate comprises a cured film on the undercoat layer. The cured film has excellent bacteria adhesion suppression performance.

The thickness of the cured film in the laminate is not particularly limited and can be determined appropriately according to the use of the laminate. For example, in a case where the base material is a denture base, the thickness of the cured film is not particularly limited and is preferably 0.01 to 10 μm.

The cured film is formed using a curable composition containing at least one compound (hereinafter, also referred to as a "specific compound") selected from the group consisting of a compound represented by Formula (I), a compound represented by Formula (II), a compound represented by Formula (IV), and a compound represented by Formula (V).

<Curable Composition>

A method of forming the cured film using the curable composition is not particularly limited and typically, the cured film can be obtained by applying the curable composition to the undercoat layer to form a curable composition layer, applying energy (heat or light) to the curable composition layer, and curing the layer. Hereinafter, each component of the curable composition will be described.

(Specific Compound)

The curable composition contains a specific compound. The content of the specific compound in the curable composition is not particularly limited and is preferably 0.1% to 99.9% by mass, more preferably 1% to 99% by mass, and even more preferably 1% to 97% by mass with respect to the total solid content of the curable composition.

The specific compound may be used alone or in combination of two or more kinds thereof. In a case where two or more kinds of specific compounds are used in combination, the total content is preferably within the above range.

Compound Represented by Formula (I)

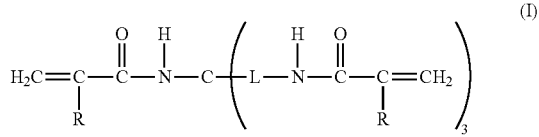

In Formula (I), R represents a hydrogen atom or a methyl group, a plurality of R's may be the same or different, L represents one group selected from the group consisting of —O—, an alkylene group having 2 to 4 carbon atoms, or a divalent linking group obtained by combining these groups, and a plurality of L's may be the same or different.

A carbon atom is preferably located at a position adjacent to the nitrogen atom in the amide group adjacent to L. That is, as the group adjacent to the nitrogen atom in the amide group, an alkylene group having 2 to 4 carbon atoms is preferably located.

Examples of the "divalent linking group obtained by combining these groups" include an alkylene group having 2 to 4 carbon atoms and containing —O—, such as —OCH$_2$CH$_2$—, —OCH$_2$CH$_2$CH$_2$—, —OCH$_2$CH$_2$CH$_2$CH$_2$—, —CH$_2$OCH$_2$—, —CH$_2$OCH$_2$CH$_2$—, or —CH$_2$OCH$_2$CH$_2$CH$_2$—, and a group expressed by —(O-alkylene group (having 2 to 4 carbon atoms))n-(n represents an integer of 2 or more; the upper limit is not particularly limited, but may be about 100). In addition, in each group exemplified as the "divalent linking group obtained by combining these groups", either of two bonding sites may be bonded to the amide group.

Among these, from the viewpoint that a laminate having the more excellent effect of the present invention can be obtained, L is preferably an alkylene group having 2 to 4 carbon atoms and containing —O—.

Compound represented by Formula (II)

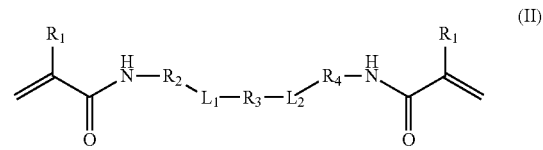

In Formula (II), $R_1$ represents a hydrogen atom or a methyl group, a plurality of $R_1$ may be the same or different, $R_2$ and $R_4$ each independently represent one group selected from the group consisting of —O—, an alkylene group having 1 to 4 carbon atoms, and divalent linking group obtained by combining these groups. In addition, it is preferable that a carbon atom is located at a position adjacent to the nitrogen atom in the amide group adjacent to $R_2$ and $R_4$. As the group adjacent to the nitrogen atom in the amide group, an alkylene group having 1 to 4 carbon atoms is preferably located.

Examples of the "divalent linking group obtained by combining these groups" include an alkylene having 1 to 4 carbon atoms and containing —O— such as —OCH$_2$—, —OCH$_2$CH$_2$—, —OCH$_2$CH$_2$CH$_2$—, —OCH$_2$CH$_2$CH$_2$CH$_2$—, —CH$_2$OCH$_2$—, —CH$_2$OCH$_2$CH$_2$—, or —CH$_2$OCH$_2$CH$_2$CH$_2$—; and —(O-alkylene group (having 1 to 4 carbon atoms))n-(n represents an integer of 2 or more; the upper limit is not particularly limited and is preferably 100 or less). In addition, in each group exemplified as the "divalent linking group obtained by combining these groups", either of two bonding sites may be bonded to the amide group.

Among these, from the viewpoint that a laminate having the more excellent effect of the present invention can be obtained, as $R_2$ and $R_4$, an alkylene group having 1 to 4 carbon atoms or an alkylene group having 1 to 4 carbon atoms and containing —O— is preferable.

$R_3$ represents one group selected from the group consisting of —O—, an alkylene group having 1 to 4 carbon atoms, a group represented by Formula (III), and a divalent linking group obtained by combining these groups.

Examples of the "divalent linking group obtained by combining these groups" include the groups described as the $R_2$ and $R_4$. In a case where the group represented by Formula (III) is combined with another group, it is preferable that an alkylene group having 1 to 4 carbon atoms is bonded to the nitrogen atom in the group represented by Formula (III).

Among these, from the viewpoint that a laminate having the more excellent effect of the present invention can be obtained, as $R_3$, an alkylene group having 1 to 4 carbon atoms, an alkylene group having 1 to 4 carbon atoms and containing —O—, or the group represented by Formula (III) is preferable.

$L_1$ and $L_2$ each independently represents a single bond or the group represented by Formula (III).

In a case where $R_3$ represents Formula (III), both $L_1$ and $L_2$ preferably represent a single bond.

In a case where in Formula (II), R3 is a group represented by Formula (III), $R_2$ and $R_4$ each may represent an alkylene group having 1 to 4 carbon atoms and $L_1$ and $L_2$ may represent a single bond.

In a case where $R_3$ is an alkylene group having 1 to 4 carbon atoms, $L_1$ and $L_2$ may represent the group represented by Formula (III), and $R_2$ and $R_4$ may each independently represent an alkylene group having 1 to 4 carbon atoms.

In a case where $R_3$ represents an alkylene group having 1 to 4 carbon atoms and containing —O— (for example, —CH$_2$OCH$_2$—), $L_1$ and $L_2$ may represent a single bond, $R_2$ and $R_4$ may each independently represent alkylene group having 1 to 4 carbon atoms and containing —O— (for example, —CH$_2$OCH$_2$CH$_2$CH$_2$—).

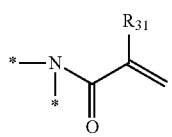
(III)

In Formula (III), $R_{31}$ represents a hydrogen atom or a methyl group, and * represents a bonding site. Usually, a carbon atom is located at *.

Specific examples of the compound represented by Formula (I) or (II) are shown below.

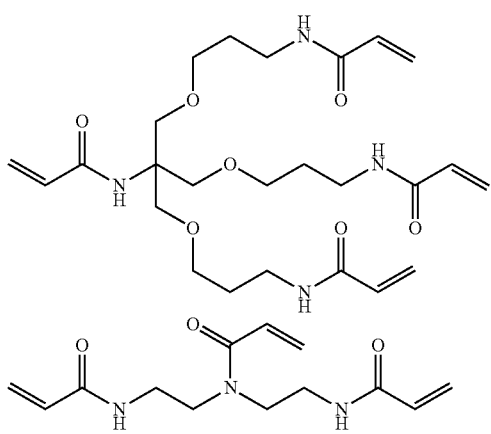

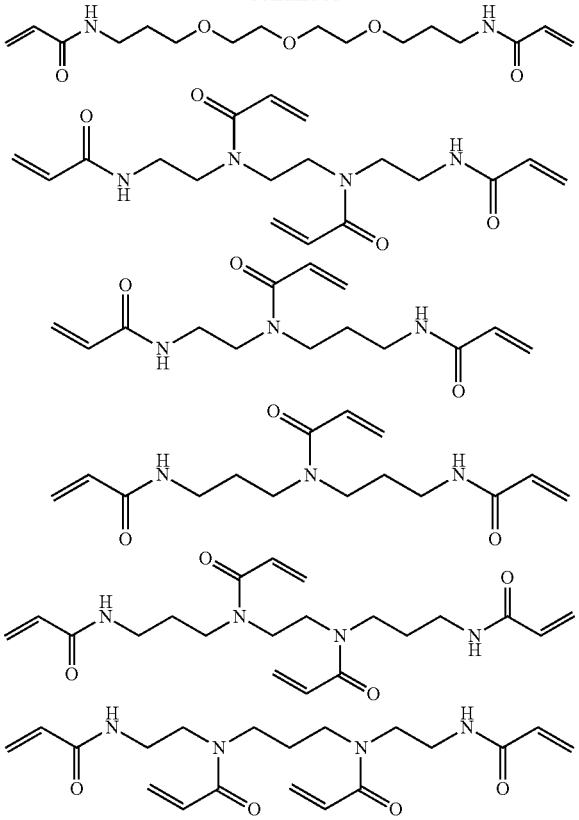

As the compound represented by Formula (I) or (II), various commercially available products can be used, and the compound can be synthesized by the method described in public technical number 2013-502654.

Compound Represented by Formula (IV)

The compound represented by Formula (IV) and Formula (V) described later is generally called betaine. Generally, betaine is a compound in which a positive charge and a negative charge are provided at positions not adjacent to each other in the same molecule, a hydrogen atom is not bonded to an atom having a positive charge, and the molecule as a whole has no charge (inner salt).

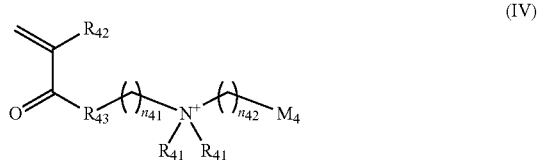
(IV)

In Formula (IV), $R_{41}$ represents one group selected from the group consisting of a methyl group, an ethyl group, an n-propyl group, and an i-propyl group, and a plurality of $R_{41}$'s may be the same or different. Among these, $R_{41}$ preferably represents the same substituent from the viewpoint of easier synthesis of the above compound. Among these, $R_{41}$ preferably represents a methyl group.

$R_{42}$ represents a hydrogen atom or a methyl group, and $R_{43}$ represents —NH— or —O—.

$n_{41}$ and $n_{42}$ each independently an integer of 1 to 4.

From the viewpoint that the compound has more excellent solubility, in a case where $M_4$ is $SO_3^-$, 3 is preferable as $n_{41}$. In a case where $M_4$ is COO$^-$, 2 is preferable as $n_{41}$.

Similarly, from the viewpoint that compound has more excellent solubility, in a case where $M_4$ is $SO_3^-$, 4 is preferable as $n_{42}$. In a case where $M_4$ is $COO^-$, 1 is preferable.

In the present specification, a betaine monomer containing $SO_3^-$ is sometimes referred to as a sulfobetaine monomer. In addition, a betaine monomer containing $COO^-$ is sometimes referred to as a carboxybetaine monomer.

In Formula (IV), $M_4$ represents $SO_3^-$ or $COO^-$. In a case where $M_4$ is $SO_3^-$, the betaine monomer corresponds to a sulfobetaine monomer. In a case where $M_4$ is $COO^-$, the betaine monomer corresponds to a carboxybetaine monomer.

Examples of the compound represented by Formula (IV) include N-(4-sulfoalkyl)-N-((meth)acryloylaminoalkyl)-N,N-dialkylammonium betaine such as N-(4-sulfobutyl)-N-(methacryloylaminopropyl)-N, or N-dimethylammonium betaine; and N-(4-sulfoalkyl)-N-((meth)acryloyloxyalkyl)-N, N-dialkylammonium betaine such as N-(3-sulfopropyl)-N-(methacryloxyethyl)-N, or N-dimethylammonium betaine.

In addition, examples of the compound represented by Formula (IV) include compounds represented by the following formulae.

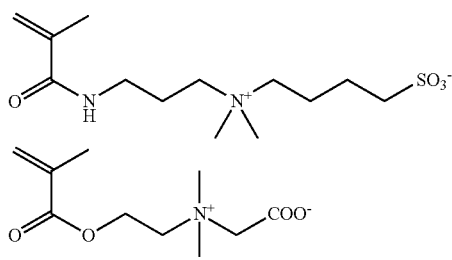

Compound Represented by Formula (V)

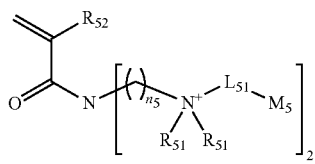

(V)

In Formula (V), $R_{51}$ represents one group selected from the group consisting of a methyl group, an ethyl group, an n-propyl group, and an i-propyl group, and a plurality of $R_{51}$'s may be the same or different. Among these, from the viewpoint of easier synthesis of the above compound, $R_{51}$ is preferably the same functional group, and $R_{51}$ is more preferably a methyl group.

$R_{52}$ represents a hydrogen atom or a methyl group.

$n_5$ represents an integer of 1 to 4. From the viewpoint that the compound has more excellent solubility, in a case where $M_5$ is $SO_3^-$ in Formula (V), $n_5$ is preferably 3. In Formula (V), two $n_5$'s may be the same or different.

$L_{51}$ represents a linear or branched alkylene group having 3 or 4 carbon atoms, and specifically includes the following structures (* represents a binding site). In addition, a plurality of $L_{51}$'s may be the same or different.

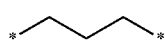

(L1)

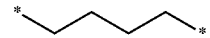

(L2)

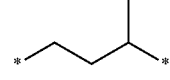

(L3)

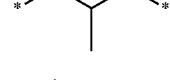

(L4)

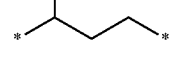

(L5)

From the viewpoint that a laminate has more excellent effect of the present invention, $L_{51}$ is preferably an n-butylene group (L2).

$M_5$ represents $SO_3^-$ or $COO^-$. In Formula (V), two $M_5$'s may be the same or different. In Formula (V), two $M_5$'s preferably represent $SO_3^-$. The compound represented by Formula (V) is preferably a compound represented by the following formula.

From the viewpoint that a laminate having more excellent effect of the present invention can be obtained, the curable composition preferably contains at least one compound selected from the group consisting of the compound represented by Formula (IV) and a compound represented by Formula (V).

From the viewpoint that a laminate having further excellent effect of the present invention can be obtained, the curable composition preferably contains at least one compound selected from the group consisting of the compound represented by Formula (I) and the compound represented by Formula (II), and at least one compound selected from the group consisting of the compound represented by Formula (IV) and the compound represented by Formula (V).

The content mass ratio of the total content of the compound represented by formula (I) and the compound represented by formula (II) with respect to the total content of the compound represented by formula (IV) and the compound represented by formula (V) is not particularly limited and from the viewpoint that a laminate having further excellent effect of the present invention can be obtained, the mass ratio is preferably 1/99 to 99/1 and more preferably 10/90 to 90/10.

(Other Components)

The curable composition may contain components other than the components described above. Other components include a polymerization initiator, a solvent, and a monomer other than the specific compound, a filler, a silane coupling agent, a polymerization inhibitor, a fragrance, a colorant, a refreshing agent, a preservative, an antibacterial agent, a binder resin, a polyfunctional amine, a polyfunctional thiol, a plasticizer, a surface lubricant, a leveling agent, a softener, an antioxidant, an anti-aging agent, a light stabilizer, an ultraviolet absorber, and a surfactant.

Polymerization Initiator

The curable composition preferably contains a polymerization initiator. The content of the polymerization initiator in the curable composition is not particularly limited and is preferably 0.01% to 50% by mass with respect to the total solid content of the curable composition. The polymerization initiator may be used alone or in combination of two or more kinds thereof. In a case where two or more kinds of polymerization initiators are used in combination, the total content is preferably within the above range. The polymerization initiator may be used in combination with a sensitizer and/or a reducing agent.

Examples of the polymerization initiator include a photopolymerization initiator and a thermal polymerization initiator. Of these, a photopolymerization initiator is preferable.

Examples of photopolymerization initiators include an alkyl phenone-based photopolymerization initiator, a methoxy ketone-based photopolymerization initiator, an acylphosphine oxide-based photopolymerization initiator (for example, 2,4,6-trimethylbenzoyl-diphenyl-phosphine oxide and bis(2,4,6-trimethylbenzoyl)-phenylphosphine oxide), a hydroxy ketone-based photopolymerization initiator (for example, IRGACURE 184; 1,2-α-hydroxyalkylphenone), an amino ketone-based photopolymerization initiator (for example, 2-methyl-1-[4-(methylthio)phenyl]-2-morpholino-propane-1-one (IRGACURE (registered trademark) 907)), an oxime-based photopolymerization initiator, and an oxyphenyl ester acetate-based photopolymerization initiator (IRGACURE (registered trademark) 754).

In addition, as the polymerization initiator, a diketone compound (for example, camphor quinone) is also preferable.

Examples of other initiators (for example, a thermal polymerization initiator) include an azo-based polymerization initiator (for example, V-50), a persulfate-based polymerization initiator, a persulfate material-based polymerization initiator, and a redox-based polymerization initiator.

The polymerization initiator is preferably contains the compound represented by Formula (VII) from the viewpoint that a laminate having more excellent effect of the present invention can be obtained. This compound functions as a so-called photopolymerization initiator.

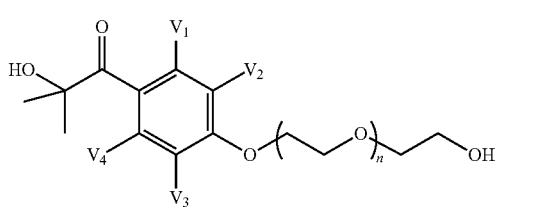

(VII)

In Formula (VII), $V_1$, $V_2$, $V_3$, and $V_4$ each independently represent a hydrogen atom or a substituent. The kind of the substituent is not particularly limited, and examples thereof include a halogen atom, an alkyl group, an alkoxy group, a hydroxy group, an alkylthio group, a mercapto group, an acyl group, and an amino group. In Formula (VII), n represents an integer of 1 to 5.

The compound represented by Formula (VII) can be synthesized by, for example, the methods described in paragraphs 0067 to 0071 and 0112 to 0115 of JP2000-186242A.

As the compound represented by Formula (VII), the compounds described in paragraphs 0063 to 0071 of WO2017/018146A can be used, and the contents are incorporated in the present specification.

For the polymerization initiator, the description after paragraph 135 of JP2010-106268A (paragraph 0163 of corresponding US2011/0124824A), the description of paragraphs 0018 to 0025 of JP2009-013115A, and the description of paragraphs 0018 to 0025 of JP2005-154312A can be referred to, and the contents are incorporated in the present specification.

For the sensitizer, the description of paragraph 154 of WO2017-086224A, and the description of paragraph 0024 of JP2005-154312A can be referred to, and the contents are incorporated in the present specification.

For the reducing agent, the description of paragraph 0025 of JP2005-154312A can be referred to and the contents are incorporated in the present specification.

Solvent

The curable composition preferably contains a solvent. Examples of the solvent include water; and organic solvents (for example, esters such as ethyl acetate and n-butyl acetate; aromatic hydrocarbons such as toluene and benzene; aliphatic hydrocarbons such as n-hexane and n-heptane; alicyclic hydrocarbons such as cyclohexane and methylcyclohexane; ketones such as methyl ethyl ketone and methyl isobutyl ketone; alcohols such as methanol and butanol; and the like). The solvents can be used alone or in combination of two or more kinds thereof.

In a case where the curable composition contains the solvent, the solid content of the curable composition is not particularly limited and is preferably 0.1% to 99% by mass and more preferably 1% to 90% by mass with respect to the total mass of the curable composition.

The solid content of the curable composition means a component that can form a cured film and does not include solvents.

Monomer Other than Specific Compound

The curable composition may further contain a monomer other than the specific compound from the viewpoint that the obtained cured film has more excellent adhesiveness to the undercoat layer and the like.

The content of the monomer other than the specific compound in the curable composition is not particularly limited, and is preferably 0.01% to 90% by mass, more preferably 20% to 80% by mass, and even more preferably 30% to 70% by mass with respect to the total solid content of the curable composition. The monomer other than the specific compound may be used alone or in combination of two or more kinds thereof. In a case where two or more kinds of polymerizable monomers are used in combination, the total content is preferably within the above range.

As the monomer other than the specific compound, monomers used in the dental field may be used and examples thereof include an aliphatic monofunctional polymerizable monomer, an aliphatic bifunctional polymerizable monomer, an aliphatic trifunctional or higher polymerizable monomer, an aromatic monofunctional polymerizable monomer, and an aromatic bifunctional polymerizable monomer.

Examples of the aliphatic monofunctional polymerizable monomer include methyl (meth)acrylate, ethyl (meth)acrylate, propyl (meth)acrylate, butyl (meth)acrylate, isobutyl (meth)acrylate, lauryl (meth)acrylate, and 2-hydroxyethyl (meth)acrylate.

Examples of the aliphatic bifunctional or higher polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, butylene glycol di(meth)acrylate, and 2,2,4-trimethylhex amethylenebi s (2-carbamoyloxyethyl)dimethacrylate.

Examples of the trifunctional or higher polymerizable monomer include trimethylolpropane tri(meth)acrylate, trimethylolethane tri(meth)acrylate, trimethylolmethane tri(meth)acrylate, tris(2-(meth)acryloxyethyl) isocyanulate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, and dipentaerythritol hexa(meth)acrylate.

Examples of the aromatic monofunctional polymerizable monomer include benzyl (meth)acrylate, phenoxyethyl (meth)acrylate, and phenoxydiethylene glycol (meth)acrylate.

Examples of the aromatic bifunctional polymerizable monomer include 2,2-bis [4-[2-hydroxy-3-(methacryloyloxy)propyloxy]phenyl]propane.

In addition, as the monomer other than the specific compound, hydrophobic monomers described in paragraphs 0035 to 0039 of JP2006-151850A can be used and the contents are incorporated in the present specification.

Further, the description in paragraphs 0018 to 0022 of JP2005-154312A can be referred to, and the contents thereof are incorporated in this specification.

Filler

The curable composition may contain a filler. The cured film formed of the curable composition containing a filler has more excellent mechanical strength and more excellent adhesiveness to the undercoat layer. The content of the filler in the curable composition is not particularly limited and is preferably 0.01% to 80% by mass, more preferably 0.05% to 50% by mass, and even more preferably 0.1% to 30% by mass with respect to the total solid content of the curable composition. The filler may be used alone or in combination of two or more kinds thereof. In a case where two or more kinds of filler are used in combination, the total content is preferably within the above range.

The average particle diameter of the filler is not particularly limited and is preferably 0.01 to 500 μm, more preferably 0.05 to 100 μm, and even more preferably 0.1 to 50 μm. The average particle size of the filler in the present specification means the average particle size measured by the Coulter method.

Examples of the filler include an organic filler, an inorganic filler, and a composite filler thereof.

Examples of a material constituting an organic filler include polymethyl methacrylate, polyethyl methacrylate, methyl methacrylate-ethyl methacrylate copolymer, crosslinked polymethyl methacrylate, crosslinked polyethyl methacrylate, polyester, polyamide, polycarbonate, polyphenylene ether, polyoxymethylene, polyvinyl chloride, polystyrene, polyethylene, polypropylene, ethylene-vinyl acetate copolymer, and acrylonitrile-styrene copolymer.

Examples of a material constituting an inorganic filler include lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoro alumino silicate glass, strontium fluoroaluminosilicate glass, barium fluoroaluminosilicate glass, and strontium calcium fluoro alumino silicate glass.

The inorganic filler may be used after being subjected to surface pretreatment with a known surface-treating agent such as a silane coupling agent.

Examples of the surface-treating agent include vinyltrimethoxysilane, vinyltriethoxysilane, vinyltrichlorosilane, vinyltri(β-methoxyethoxy)silane, 3-methacryloyloxypropyltrimethoxy silane, 11-methacryloyloxyundecyltrimethoxysilane, 3-glycidoxypropyltrimethoxysilane, 3-mercaptopropyltrimethoxysilane, and 3-aminopropyltriethoxysilane. The surface-treating agent may be used alone or in combination of two or more kinds thereof.

The composite filler is not particularly limited and examples thereof include those obtained by adding a monomer to the inorganic filler in advance, making the mixture into a paste state, and then polymerizing and pulverizing the resultant. Examples of the composite filler include a TMPT filler (obtained by mixing trimethylolpropane methacrylate and a silica filler and then polymerizing and pulverizing the mixture) and inorganic fine particles whose surface is modified by alkoxysilane having an unsaturated double bond described in JP2005-154312A.

Silane Coupling Agent

The curable composition may further contain a silane coupling agent.

The content of the silane coupling agent in the curable composition is not particularly limited and is preferably 0.01% to 50% by mass, more preferably 0.05% to 30% by mass, and even more preferably 0.1% to 20% by mass with respect to the total solid content of the curable composition. The silane coupling agent may be used alone or in combination of two or more kinds thereof. In a case where two or more kinds of silane coupling agents are used in combination, the total content is preferably within the above range.

The silane coupling agent is not particularly limited and a known silane coupling agent can be used. Examples of the silane coupling agent include silane coupling agents described in paragraph 0058 of JP2015-214514A, and the above contents are incorporated in the present specification.

[Other Layers]

The laminate according to the embodiment of the present invention may comprises the base material, the undercoat layer, and the cured film in this order described above, and may further have other layers. Other layers are not particularly limited, but examples include mixed layers.

In a case where the laminate has a mixed layer, it is preferable that the mixed layer is between the base material and the undercoat layer and/or between the undercoat layer and the cured film.

<Mixed Layer>

The mixed layer is a layer formed by mixing the respective components of the base material and the undercoat layer, or the undercoat layer and the cured film described above. In a case where the laminate has the mixed layer, the adhesiveness between layers (between the base material and the undercoat layer, and/or between the undercoat layer and the cured film) is further improved and as a result, the laminate has the more excellent effect of the present invention.

In the mixed layer, the form of mixing the components of two different layers is not particularly limited. The mixed layer may be a layer formed by mixing the components of two layers at the molecular level (in other words, a layer formed by compatibilizing two layers) or a layer formed by mixing the components of two layers in a state in which the components of the two layers are not compatible. The layer formed by mixing the components of two layers in a state in which the components of the two layers are not compatible may be a layer formed by incorporating the component of the other layer so as bite into unevenness formed of the component of one layer.

[Method for Producing Laminate]

A method for producing the laminate is not particularly limited and known production methods can be used. Among these, from the viewpoint that the base material, the undercoat layer, and the cured film are more closely attached and as a result, a laminate having the more excellent effect of the present invention can be easily obtained, the production method preferably has the following steps in the following order.

Step of forming a first coating film on a base material using an undercoat layer forming composition containing a predetermined polymer (first coating film forming step)

Step of forming a second coating film on the first coating film using a curable composition containing a specific compound (second coating film forming step)

Step of applying energy to the first coating film and the second coating film and curing the films to obtain an undercoat layer and a cured film (energy applying step)

Hereinafter, embodiments of each step will be described will be described.

[First Coating Film Forming Step]

The first coating film forming step is a step of forming a first coating film on the base material using an undercoat layer forming composition containing a predetermined polymer.

The base material that can be used in the step is not particularly limited and a known base material can be used. The embodiment is as already described as the base material that laminate has.

The form of the undercoat layer forming composition is as already described above.

The method of forming the first coating film on the base material is not particularly limited and known methods can be used. Typically, the method of applying the undercoat layer forming composition to the base material to obtain the first coating film, and if required, removing a solvent from the first coating film may be used.

The method of applying the undercoat layer forming composition to the base material is not particularly limited and known methods can be used. For example, bar coater coating, spin coating, spray coating, and curtain coating may be used.

In a case where the undercoat layer forming composition contains a solvent, it is preferable to remove the solvent from the first coating film. The method of removing the solvent is not particularly limited and known methods can be used. Typically, a method of heating the first coating film may be used. In a case of heating the first coating film, the heating temperature is preferably 40° C. to 120° C. and the heating time is preferably 10 to 120 minutes.

[Curable Composition Layer Forming Step]

The curable composition layer forming step is a step of forming a second coating film on the first coating film using a curable composition containing a specific compound.

The form of the curable composition is as already described above. The method of forming the second coating film on the first coating film is not particularly limited and known methods can be used.

Typically, a method of applying a curable composition to the first coating film may be used. Examples of the method of applying the curable composition include roll coating, kiss roll coating, gravure coating, reverse coating, roll brushing, spray coating, dip roll coating, bar coating, knife coating, air knife coating, curtain coating, lip coating, and die coating.

The second coating film may be heated. A method of heating the second coating film is not particularly limited and for example, a blast dryer, an oven, an infrared dryer or a heating drum can be used.

The heating temperature is not particularly limited and is preferably 30° C. to 150° C. and more preferably 40° C. to 120° C. The heating time is not particularly limited, and drying in the coating device is preferably 1 to 20 minutes.

[Energy Applying Step]

The energy applying step is a step of applying the first coating film and the second coating film and curing the films to obtain an undercoat layer and a cured film.

The method of applying energy to the first coating film and the second coating film is not particularly limited, and known methods can be used. For example, heating and light irradiation can be used.

The method of light irradiation is not particularly limited and for example, methods using a low pressure mercury lamp, a medium pressure mercury lamp, a high pressure mercury lamp, a metal halide lamp, deep ultraviolet light, a xenon lamp, a chemical lamp, and a carbon lamp can be used. The energy of light irradiation is not particularly limited, but is preferably 0.1 to 10 J/cm$^2$.

In addition, in a case of heating, the heating temperature is preferably 50° C. to 150° C. and the heating time is preferably 10 to 180 minutes.

[Use of Laminate]

The laminate is preferably used as a device used by being transplanted and arranged in a human living body placed in the body. Examples of the above device include artificial joints, artificial bones, artificial blood vessels, stents, dental implants, and denture bases, and among these, a denture base is preferable. That is, a laminate in which the base material is a denture base (a denture base with a coating layer) is preferable.

Since the laminate has the undercoat layer and further has the cured film, which is a firm crosslinked film, on the surface, the laminate has excellent coloration resistance and excellent thermal cycling resistance.

Therefore, particularly, in a case where the base material is a denture base, even in a case where the laminate is placed in the mouth for a long period of time, the laminate also has excellent properties that the cured film is not easily peeled off and the physical properties and the tone of the cured film are not easily changed.

The coloration resistance represents properties that even in a case where coloring foods to eat and drink in daily life (for example, black tea, green tea, coffee, red wine, and curry) are repeatedly consumed, mainly, the tone of the surface of the laminate is not easily changed. In addition, the thermal cycling resistance represents properties that the physical properties of the laminate, such as adhesiveness and wear resistance, are not easily changed before and after the heat cycling test in response to the temperature change in the mouth associated with eating and drinking in daily life.

[Kit]

A kit according to an embodiment of the present invention is formed of the above-described undercoat layer forming composition and curable composition.

In the kit, the undercoat layer forming composition and the curable composition may be accommodated in separate containers. That is, the kit is preferably a kit containing a first container including a container, and the undercoat layer forming composition accommodated in the container, and a second container including a container separate from the above container and the curable composition accommodated in the other container.

The container is not particularly limited, and a known container can be used. The capacity, shape, and the like of the container can be appropriately determined according to the use.

The kit is preferably used to produce the laminate (in other words, provided to produce the laminate). Of these, in a case where the base material is a denture base, a denture base with a coating layer having an undercoat layer and a cured film on the denture base can be easily obtained, and thus this case is preferable.

The denture base with a coating layer has excellent bacteria adhesion suppression performance and the bacteria adhesion suppression performance is maintained for a long period of time.

EXAMPLES

Hereinafter, the present invention will be described in more detail based on examples. The materials, amounts used, ratios, treatment details, treatment procedures, and the like shown in the following examples can be changed as appropriate without departing from the spirit of the present invention. Therefore, the scope of the present invention should not be construed as being limited by the following examples.

(Preparation of Undercoat Layer Forming Composition)

The content of each of undercoat layer forming compositions 1 to 4 was adjusted with methyl ethyl ketone such that the content of each of the following polymers with respect to the total mass of the undercoat layer forming composition was 9.7% by mass, and the content of IRGACURE 2959 (BASF, "Irg 2959", hereinafter, corresponding to a polymerization initiator) with respect to the total mass of the undercoat layer forming composition was 0.3% by mass. In addition, the numerical value described in each repeating unit represents the copolymerization ratio (molar ratio).

Undercoat layer forming composition 1 (containing following polymer A1)

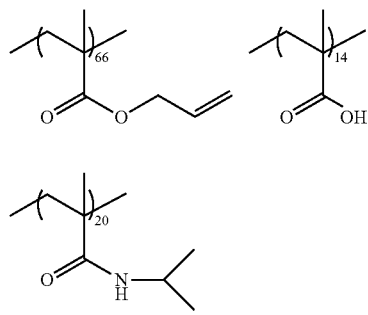

Undercoat layer forming composition 2 (containing following polymer A2)

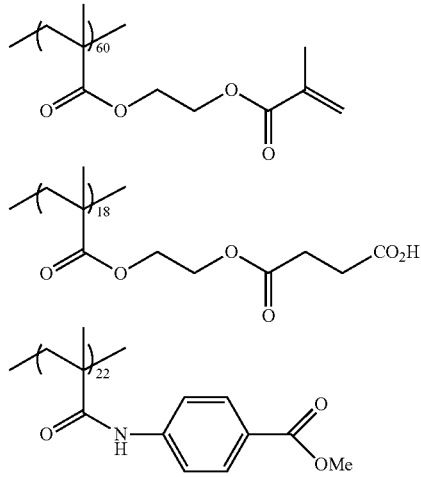

Undercoat layer forming composition 3 (containing following polymer A3)

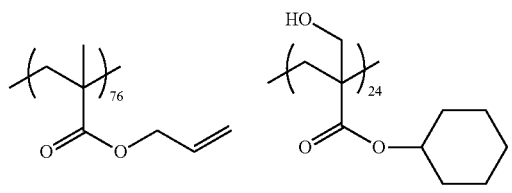

Undercoat layer forming composition 4 (containing following polymer A4)

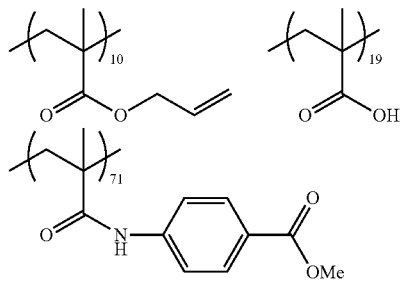

Undercoat layer forming composition 5 (containing following polymer A5)

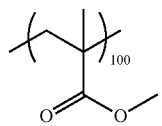

Each polymer was synthesized by the following method.

Synthesis Example of Polymer A1

Into a 500 ml three-necked flask, 13.52 g of propylene glycol monomethyl ether (MFG) was poured and the internal temperature was set to 70° C. A monomer solution including 3.61 g of methacrylic acid, 24.98 g of allyl methacrylate, 7.63 g of N-isopropylmethacrylamide, 0.461 g of V-601 (radical polymerization initiator, manufactured by Wako Pure Chemical Corporation), and 54.08 g of MFG was prepared and added dropwise into the reaction container for 2 hours. After the completion of the dropwise addition of the monomer solution, the reaction solution was stirred for 2 hours, and the initiator was added (0.461 g of V-601). Next, immediately after the initiator was added, the temperature was raised to 85° C., the reaction solution was stirred for 2 hours, and then allowed to cool to obtain the desired polymer.

Polymers A2 to A4 were synthesized in the same manner as the synthetization of the polymer A1 while changing the kinds of the repeating units and the compositional ratio of the repeating units.

For a polymer A5, a polymethyl methacrylate (81503, manufactured by Sigma-Aldrich) was used.

(Preparation of Curable Composition)

Each of the following compounds was mixed with IRGA-CURE 2959 (BASF, hereinafter "Irg 2959", corresponding to the polymerization initiator) in the composition shown in Table 1 to prepare each curable composition. The numerical values in Table 1 represent the content (% by mass) of each component with respect to the total solid content of the curable composition. In addition, the solid content of each curable composition was adjusted to be 20% by mass with methanol.

Compound B1

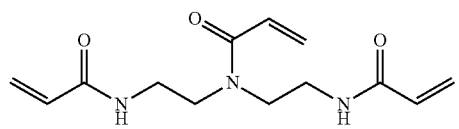

Compound B2

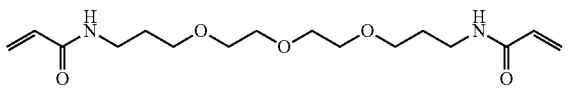

Compound B3

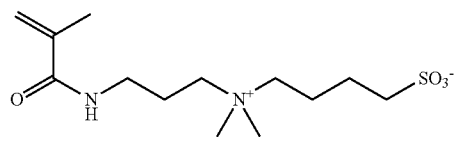

Compound B4

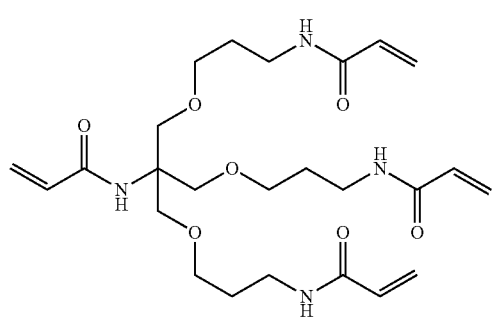

-continued

Compound B5

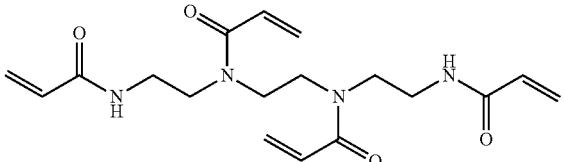

Compound B6

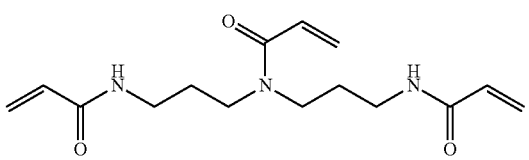

(Adhesiveness Test)

As a base material imitating a denture base, a denture base (corresponds to the base material) was prepared by a wet heating polymerization method usually performed using an acrylic resin for a denture base (ISO Resin•H, DENKEN-HIGHDENTAL Co., Ltd.). Next, the undercoat layer forming composition was applied to the denture base so that the thickness of the undercoat layer was 1 μm, and the solvent was removed to obtain a denture base with a first coating film. Next, the curable composition was applied to the denture base with the first coating film so that the thickness of the cured film was 3 μm, and a denture base with a second coating film was obtained. Next, the denture base with the second coating film was exposed using an ultraviolet (UV) exposure machine "ECS-401G (product name)", manufactured by Eye Graphics Co., Ltd. (light source: a high pressure mercury lamp) at an exposure amount of 4 $J/cm^2$ and the first coating film and the second coating film were cured to obtain an undercoat layer and a cured film respectively. The denture base with a coating layer (corresponding to a laminate comprising an undercoat layer and a cured film on a base material in this order) was obtained.

Next, the denture base with the coating layer was immersed in a phosphate buffered saline (PBS) solution, and taken out after 24 hours had passed at 37° C. to evaluate adhesiveness from the area of the coating layer remaining on the denture base. The area of the coating layer remaining on the denture base relative to the surface area of the denture base was expressed as a percentage as a coating rate and evaluated according to the following standards.

A: The coating rate was 90% or higher.
B: The coating rate was 70% or higher and lower than 90%.
C: The coating rate was 50% or more and lower than 70%.
D: The coating rate was lower than 50%.

(Bacteria Adhesion Suppression Performance Test)

The test piece prepared in the adhesiveness test was cut into a 1 cm square and placed in a 24 well plate. In each well, 1 ml each of a test solution in which a yeast cell of *C. albicans* (JCM2085, JCM is an abbreviation for Japan Collection of Microorganisms) was inoculated in a yeast extract peptone dextrose (YPD) medium and the cell concentration was adjusted to be 970 cell/ml was put.

Next, the 24 well plate containing the test piece and the test solution was cultured at 37° C. for 36 hours under aerobic conditions. Next, after washing the test piece after cultivation with a phosphate buffered saline (PBS) buffer solution, the number of bacteria adhering to the test piece was determined by a colorimetric determination method (XTT method; XTT is an abbreviation of 2,3-Bis-(2-Methoxy-4-Nitro-5-Sulfophenyl)-2H-Tetrazolium-5-Carboxanilide). The light absorbance of the base material having no undercoat layer and no cured film was set to a reference, and a difference in light absorbance with each test piece (reduction rate of light absorbance) was obtained and evaluated based on the following standards.

A: The difference from the reference was more than 30%.
B: The difference from the reference was 20% or more and less than 30%.
C: The difference from the reference was 10% or more and less than 20%.
D: The difference from the reference was less than 10%.

more excellent bacteria adhesion suppression performance compared to the laminate of Example 1.

Further, the laminate of Example 1 comprising the undercoat layer formed of the undercoat layer forming composition in which double bond equivalent of the polymer was 2000 or less had more excellent adhesiveness compared to the laminate of Example 6.

The laminate of Example 7 comprising the cured film formed of the curable composition containing both the compound represented by Formula (II) and the compound represented by Formula (IV) had more excellent adhesiveness and bacteria adhesion suppression performance compared to the laminate of Example 1.

TABLE 1

| | Undercoat layer | | | | Cured film | | | | | | | Evaluation | |
|---|---|---|---|---|---|---|---|---|---|---|---|---|---|
| | Undercoat layer forming composition | Polymer | | | Component of Curable composition (% by mass) | | | | | | | | Bacteria adhesion suppression performance |
| | | | | | Specific compound | | | | | | Polymerization initiator | | |
| | Kind | Kind | Double bond equivalent | Acid value | Hydroxyl number | B1 | B2 | B3 | B4 | B5 | B6 | Irg 2959 | Adhesiveness | |
| Example 1 | 1 | A1 | 183 | 62 | | 97 | | | | | | 3 | B | C |
| Example 2 | 1 | A1 | 183 | 62 | | | 97 | | | | | 3 | B | B |
| Example 3 | 1 | A1 | 183 | 62 | | | | 97 | | | | 3 | B | A |
| Example 4 | 2 | A2 | 359 | 45 | | 97 | | | | | | 3 | B | C |
| Example 5 | 3 | A3 | 184 | | 96 | 97 | | | | | | 3 | B | C |
| Example 6 | 4 | A4 | 2054 | 52 | | 97 | | | | | | 3 | C | C |
| Example 7 | 1 | A1 | 183 | 62 | | | 29.1 | 67.9 | | | | 3 | A | A |
| Example 8 | 1 | A1 | 183 | 62 | | | | | 97 | | | 3 | B | C |
| Example 9 | 1 | A1 | 183 | 62 | | | | | | 97 | | 3 | B | C |
| Example 10 | 1 | A1 | 183 | 62 | | | | | | | 97 | 3 | B | C |
| Comparative Example 1 | None | | | | | | 97 | | | | | 3 | D | D |
| Comparative Example 2 | None | | | | | | | | | | | | No evaluation | D |
| Comparative Example 3 | 5 | A5 | 0 | | | | 97 | | | | | 3 | D | D |

In the table, "Component of curable composition (% by mass)" represents % by mass of each component with respect to the total solid content of the curable composition.

Also, "None" in the column "Undercoat layer forming composition" indicates that no undercoat layer was provided. In addition, the blank in the column "Curable composition" indicates that the corresponding component was not used. Further, "No evaluation" in the evaluation column "Adhesiveness" of Comparative Example 2 indicates that the Adhesiveness test could not be performed.

From the results shown in Table 1, the laminates of Examples 1 to 10 had the effects of the present invention. On the other hand, the laminates of Comparative Examples 1 to 3 did not have the effect of the present invention.

In addition, the laminate of Example 3 comprising the cured film formed of the curable composition including the specific compound formed of the compound represented by Formula (IV) had more excellent bacteria adhesion suppression performance compared to the laminate of Example 2 comprising the cured film formed of the curable composition including the specific compound formed of the compound represented by Formula (II).

In addition, the laminate of Example 2 comprising the cured film formed of the curable composition in which the specific compound was formed of the compound represented by Formula (II) and $R_3$ in Formula (II) was an alkylene group having 1 to 4 carbon atoms and containing —O— had (Rub Resistance Test in Wet Environment)

A denture base with a coating layer (corresponding to a laminate in which an undercoat layer and a cured film are provided on the base material in this order) was obtained in the same manner as the test piece for the adhesiveness test.

Next, using a microtribology testing machine (UMT-3) manufactured by Bruker AXS GmbH and a toothbrush ("G.U.M dental brush #191 (product name)") with "normal" hardness, a 2 ml PBS buffer solution was added dropwise to the toothbrush, and under the conditions that the gliding speed of 60 times/min, a load of 200 g, and a stroke width of 3 mm, each sample was brushed for 300 seconds, and the rub resistance was evaluated from the state of the coating layer on the denture base in the wet environment. The coating layer on the denture base was visually observed and evaluated according to the following standards. The results are shown in Table 2.

A: Changes were not observed in the coating layer.
B: Changes such as scratches were observed in the coating layer.

TABLE 2

| | Rub resistance test in wet environment |
|---|---|
| Example 1 | A |
| Example 2 | A |

TABLE 2-continued

| | Rub resistance test in wet environment |
|---|---|
| Example 3 | A |
| Example 4 | A |
| Example 5 | A |
| Example 6 | A |
| Example 8 | A |
| Example 9 | A |
| Example 10 | A |
| Comparative Example 1 | B |
| Comparative Example 3 | B |

From the results shown in Table 2, it was found that the laminates of Examples 1 to 6 and Examples 8 to 10 had excellent rub resistance in a wet environment. On the other hand, the laminates of Comparative Examples 1 and 3 did not have rub resistance in a wet environment.

What is claimed is:

1. A laminate comprising, in order:
a base material;
an undercoat layer formed of an undercoat layer forming composition containing a polymer containing a repeating unit containing a polymerizable group and a repeating unit containing a polar group; and
a cured film formed of a curable composition containing at least one compound selected from the group consisting of a compound represented by Formula (I), a compound represented by Formula (II), a compound represented by Formula (IV), and a compound represented by Formula (V),

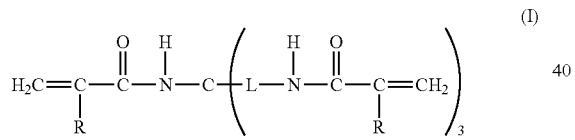

(I)

in Formula (I), R represents a hydrogen atom or a methyl group, a plurality of R's may be the same or different, L represents one group selected from the group consisting of —O—, an alkylene group having 2 to 4 carbon atoms, or a divalent linking group obtained by combining these groups, and a plurality of L's may be the same or different,

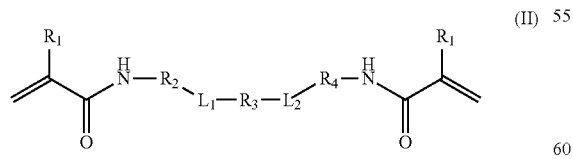

(II)

in Formula (II), $R_1$ represents a hydrogen atom or a methyl group, a plurality of $R_1$ may be the same or different, $R_2$ and $R_4$ each independently represent one group selected from the group consisting of —O—, an alkylene group having 1 to 4 carbon atoms, and a divalent linking group obtained by combining these groups, $R_3$ represents one group selected from the group consisting of —O—, an alkylene group having 1 to 4 carbon atoms, a group represented by Formula (III), and a divalent linking group obtained by combining these groups, and $L_1$ and $L_2$ each independently represents a single bond or the group represented by Formula (III),

(III)

in Formula (III), $R_{31}$ represents a hydrogen atom or a methyl group, and * represents a bonding site,

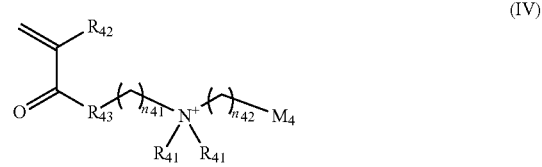

(IV)

in Formula (IV), $R_{41}$ represents one group selected from the group consisting of a methyl group, an ethyl group, an n-propyl group, and an i-propyl group, a plurality of $R_{41}$'s may be the same or different, $R_{42}$ represents a hydrogen atom or a methyl group, $R_{43}$ represents —NH— or —O—, $n_{41}$ and $n_{42}$ each independently represent an integer of 1 to 4, and $M_4$ represents $SO_3^-$ or $COO^-$, and

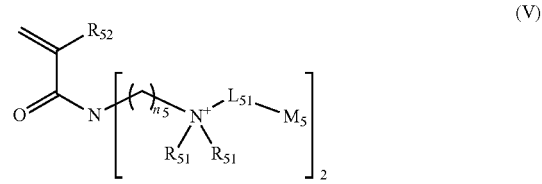

(V)

in Formula (V), $R_{51}$ represents one group selected from the group consisting of a methyl group, an ethyl group, an n-propyl group, and an i-propyl group, a plurality of $R_{51}$'s may be the same or different, $R_{52}$ represents a hydrogen atom or a methyl group, $n_5$ represents an integer of 1 to 4, $L_{51}$ represents a linear or branched alkylene group having 3 or 4 carbon atoms, and $M_5$ represents $SO_3^-$ or $COO^-$.

2. The laminate according to claim 1,
wherein a double bond equivalent of the polymer is 2000 or less.

3. The laminate according to claim 1,
wherein the repeating unit containing a polymerizable group is a repeating unit represented by Formula (A1),

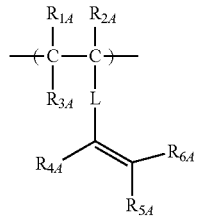

(A1)

in Formula (A1), $R_{1A}$, $R_{2A}$, and $R_{3A}$ each independently represent one group selected from the group consisting of a hydrogen atom, an alkyl group having 1 to 6 carbon atoms, and a halogen atom, $R_{4A}$ to $R_{6A}$ each independently represent one group selected from the group consisting of a hydrogen atom, an alkyl group having 1 to 6 carbon atoms, a halogen atom, an acyl group, and an acyloxy group, $R_{4A}$ and $R_{5A}$ or $R_{5A}$ and $R_{6A}$ may each form a ring, and L represents one group selected from the group consisting of —CO—, —O—, —NH—, a divalent aliphatic group, a divalent aromatic group, and a divalent linking group obtained by combining these groups.

4. The laminate according to claim 1,
wherein an acid value or a hydroxyl number of the polymer is 20 mgKOH/g or more.

5. The laminate according to claim 1,
wherein the curable composition contains at least one compound selected from the group consisting of the compound represented by Formula (I) and the compound represented by Formula (II), and at least one compound selected from the group consisting of the compound represented by Formula (IV) and the compound represented by Formula (V).

6. The laminate according to claim 5,
wherein a content ratio of a total content of the compound represented by Formula (I) and the compound represented by Formula (II) with respect to a total content of the compound represented by Formula (IV) and the compound represented by Formula (V) is 10/90 to 90/10.

7. The laminate according to claim 1,
wherein the curable composition further contains a polymerization initiator.

8. The laminate according to claim 1,
wherein the base material is a denture base.

9. The laminate according to claim 2,
wherein the repeating unit containing a polymerizable group is a repeating unit represented by Formula (A1),

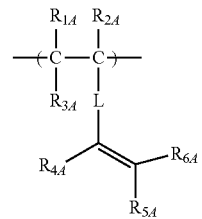

(A1)

in Formula (A1), $R_{1A}$, $R_{2A}$, and $R_{3A}$ each independently represent one group selected from the group consisting of a hydrogen atom, an alkyl group having 1 to 6 carbon atoms, and a halogen atom, $R_{4A}$ to $R_{6A}$ each independently represent one group selected from the group consisting of a hydrogen atom, an alkyl group having 1 to 6 carbon atoms, a halogen atom, an acyl group, and an acyloxy group, $R_{4A}$ and $R_{5A}$ or $R_{5A}$ and $R_{6A}$ may each form a ring, and L represents one group selected from the group consisting of —CO—, —O—, —NH—, a divalent aliphatic group, a divalent aromatic group, and a divalent linking group obtained by combining these groups.

10. The laminate according to claim 2,
wherein an acid value or a hydroxyl number of the polymer is 20 mgKOH/g or more.

11. The laminate according to claim 3,
wherein an acid value or a hydroxyl number of the polymer is 20 mgKOH/g or more.

12. The laminate according to claim 2,
wherein the curable composition contains at least one compound selected from the group consisting of the compound represented by Formula (I) and the compound represented by Formula (II), and at least one compound selected from the group consisting of the compound represented by Formula (IV) and the compound represented by Formula (V).

13. The laminate according to claim 3,
wherein the curable composition contains at least one compound selected from the group consisting of the compound represented by Formula (I) and the compound represented by Formula (II), and at least one compound selected from the group consisting of the compound represented by Formula (IV) and the compound represented by Formula (V).

14. The laminate according to claim 4,
wherein the curable composition contains at least one compound selected from the group consisting of the compound represented by Formula (I) and the compound represented by Formula (II), and at least one compound selected from the group consisting of the compound represented by Formula (IV) and the compound represented by Formula (V).

15. The laminate according to claim 3,
wherein the base material is a denture base.

16. The laminate according to claim 6,
wherein the base material is a denture base.

* * * * *